US012419901B2

(12) United States Patent
DiPietro

(10) Patent No.: US 12,419,901 B2
(45) Date of Patent: *Sep. 23, 2025

(54) PRODRUGS OF DEOXYNUCLEOSIDES FOR TREATMENT OF DISEASES CAUSED BY UNBALANCED NUCLEOTIDE POOLS

(71) Applicant: UCB BIOSCIENCES, INC., Morrisville, NC (US)

(72) Inventor: Daniel DiPietro, Brooklyn, NY (US)

(73) Assignee: UCB BIOSCIENCES, INC., Morrisville, NC (US)

( * ) Notice: Subject to any disclaimer, the term of this patent is extended or adjusted under 35 U.S.C. 154(b) by 141 days.

This patent is subject to a terminal disclaimer.

(21) Appl. No.: 18/167,308

(22) Filed: Feb. 10, 2023

(65) Prior Publication Data

US 2023/0181616 A1  Jun. 15, 2023

Related U.S. Application Data

(63) Continuation of application No. 17/046,865, filed as application No. PCT/US2019/027364 on Apr. 12, 2019, now Pat. No. 11,628,182.

(60) Provisional application No. 62/656,861, filed on Apr. 12, 2018.

(51) Int. Cl.
  *A61K 31/7076* (2006.01)
  *A61K 31/7072* (2006.01)
  *A61P 43/00* (2006.01)
  *A61K 9/00* (2006.01)

(52) U.S. Cl.
  CPC ...... *A61K 31/7076* (2013.01); *A61K 31/7072* (2013.01); *A61P 43/00* (2018.01); *A61K 9/0053* (2013.01)

(58) Field of Classification Search
  CPC .............. A61K 31/7072; A61K 31/7076
  See application file for complete search history.

(56) References Cited

U.S. PATENT DOCUMENTS

| | | | |
|---|---|---|---|
| 5,432,272 A | 7/1995 | Benner | |
| 6,875,751 B2 | 4/2005 | Imbach et al. | |
| 7,125,855 B2 | 10/2006 | Bhat et al. | |
| 10,292,996 B2 | 5/2019 | Hirano et al. | |
| 10,471,087 B2 | 11/2019 | Hirano et al. | |
| 2016/0279159 A1 | 9/2016 | Hirano et al. | |
| 2021/0077519 A1 | 3/2021 | DiPietro | |

FOREIGN PATENT DOCUMENTS

| | | |
|---|---|---|
| EP | 0753525 A1 | 1/1997 |
| WO | WO-0196353 A2 | 12/2001 |
| WO | WO-2016205671 A1 | 12/2016 |
| WO | WO-2017087517 A1 | 5/2017 |
| WO | WO-2017223421 A1 | 12/2017 |

OTHER PUBLICATIONS

International Search Report and Written Opinion for Int'l Application No. PCT/US2019/027364, Korean Intellectual Property Office, Republic of Korea, mailed on Aug. 2, 2019, 12 pages.
Casanova, E., et al., "5'-Trityl-substituted thymidine derivatives as a novel class of antileishmanial agents: Leishmania infantum EndoG as a potential target," ChemMedChem. 8(7):1161-1174, Wiley-VCH, Germany (2013).
Tsao, Y.T., et al., "Regioisomeric Preference in Ring-Opening Polymerization of 3',5'-Cyclic Phosphoesters of Functional Thymidine DNA Analogues," ACS Macro. Lett. 7(2): 153-158, American Chemical Society, United States (2018).
Akman, H.O., et al., "Thymidine Kinase 2 (H126N) Knockin Mice Show the Essential Role of Balanced Deoxynucleotide Pools for Mitochondrial DNA Maintenance," Human Molecular Genetics 17(16):2433-2440, IRL Press at Oxford University Press, United Kingdom (Aug. 2008).
Alston, C.L., et al., "Late-onset Respiratory Failure Due to TK2 Mutations Causing Multiple mtDNA Deletions," Neurology 81(23):2051-2053, Lippincott Williams & Wilkins, United States (Dec. 2013).
Bartesaghi, S., et al., "Loss of Thymidine Kinase 2 Alters Neuronal Bioenergetics and Leads to Neurodegeneration," Human Molecular Genetics 19(9):1669-1677, IRL Press at Oxford University Press, United Kingdom (May 2010).
Behin, A., et al., "Adult Cases of Mitochondrial DNA Depletion Due to TK2 Defect: An Expanding Spectrum," Neurology 78(9):644-648, Lippincott Williams & Wilkins, United States (Feb. 2012).
Blakely, E., et al., "Novel Mutations in the TK2 Gene Associated With Fatal Mitochondrial DNA Depletion Myopathy," Neuromuscular disorders: NMD 18(7):557-560, Pergamon Press, United Kingdom (Jul. 2008).
Bourdon, A., et al., "Mutation of RRM2B, Encoding P53-Controlled Ribonucleotide Reductase (P53R2), Causes Severe Mitochondrial DNA Depletion," Nature Genetics 39(6):776-780, Nature Pub. Co., United States (Jun. 2007).
Camara, Y., et al., "Feeding the Deoxyribonucleoside Salvage Pathway to Rescue Mitochondrial DNA," Drug Discovery Today 18(19-20):950-957, Elsevier Science Ltd., United Kingdom (Oct. 2013).
Camara, Y., et al., "Administration of Deoxyribonucleosides or Inhibition of Their Catabolism as a Pharmacological Approach for Mitochondrial DNA Depletion Syndrome," Human Molecular Genetics 23(9):2459-2467, IRL Press at Oxford University Press, United Kingdom (May 2014).
Carrozzo, R., et al., "Mutation Analysis in 16 Patients With mtDNA Depletion," Human Mutation 21(4):453-454, Wiley-Liss, United States (Apr. 2003).
Chanprasert, S., et al., "Molecular and Clinical Characterization of the Myopathic Form of Mitochondrial DNA Depletion Syndrome Caused by Mutations in the Thymidine Kinase (TK2) Gene," Molecular Genetics and Metabolism 110(1-2):153-161, Academic Press, United States (Sep. 2013).

(Continued)

*Primary Examiner* — Bahar Craigo
(74) *Attorney, Agent, or Firm* — STERNE, KESSLER, GOLDSTEIN & FOX P.L.L.C.

(57) ABSTRACT

Deoxynucleotide prodrugs for treatment of diseases characterized by unbalanced nucleotide pools are provided herein.

21 Claims, No Drawings

(56) References Cited

OTHER PUBLICATIONS

Collins, J., et al., "Progressive Myofiber Loss With Extensive Fibro-fatty Replacement in a Child With Mitochondrial DNA Depletion Syndrome and Novel Thymidine Kinase 2 Gene Mutations," Neuromuscular Disorders: NMD 19(11):784-787, Pergamon Press, United Kingdom (Nov. 2009).
Copeland, W.C., "Inherited Mitochondrial Diseases of DNA Replication," Annual Review of Medicine 59:131-146, Annual Reviews, United States (2008).
Dimauro, S. and Hirano, M., "Mitochondrial Encephalomyopathies: An Update," Neuromuscular Disorders: NMD 15(4):276-286, Pergamon Press, United Kingdom (Apr. 2005).
Dimauro, S. and Schon, E.A., "Mitochondrial Respiratory-chain Diseases," The New England Journal of Medicine 348(26):2656-2668, Massachusetts Medical Society, United States (Jun. 2003).
El-Hattab, A. W., et al., "MPV17-related Mitochondrial DNA Maintenance Defect: New Cases and Review of Clinical, Biochemical, and Molecular Aspects," Human Mutation 39(4):461-470, Wiley-Liss, United States (Apr. 2018).
Elpeleg, O., et al., "Deficiency of the ADP-Forming Succinyl-CoA Synthase Activity is Associated With Encephalomyopathy and Mitochondrial DNA Depletion," American Journal of Human Genetics 76(6):1081-1086, Cell Press, United States (Jun. 2005).
Galbiati, S., et al., "New Mutations in TK2 Gene Associated With Mitochondrial DNA Depletion," Pediatric Neurology 34(3):177-185, Elsevier Science Publishing, United States (Mar. 2006).
Garone, C., et al., "MPV17 Mutations Causing Adult-Onset Multisystemic Disorder With Multiple Mitochondrial DNA Deletions," Archives of Neurology 69(12):1648-1651, American Medical Association, United States (Dec. 2012).
Goethem, G.V., et al., "Mutation of POLG is Associated With Progressive External Ophthalmoplegia Characterized by mtDNA Deletions," Nature Genetics 28(3):211-212, Nature Pub. Co., United States (Jul. 2001).
Gotz, A., et al., "Thymidine Kinase 2 Defects Can Cause Multi-tissue mtDNA Depletion Syndrome," Brain: A Journal of Neurology 131(Pt 11):2841-2850, Oxford University Press, England (Nov. 2008).
Hirano, M., et al., "Defects of Intergenomic Communication: Autosomal Disorders That Cause Multiple Deletions and Depletion of Mitochondrial DNA," Seminars in Cell & Developmental Biology 12(6):417-427, Academic Press, United Kingdom (Dec. 2001).
Leshinsky-Silver, E., et al., "A Defect in the Thymidine Kinase 2 Gene Causing Isolated Mitochondrial Myopathy Without mtDNA Depletion," European Journal of Paediatric Neurology 12(4):309-313, Saunders, United Kingdom (Jul. 2008).
Lesko, N., et al., "Two Novel Mutations in Thymidine Kinase-2 Cause Early Onset Fatal Encephalomyopathy and Severe mtDNA Depletion," Neuromuscular Disorders 20(3):198-203, Pergamon Press, United Kingdom (Mar. 2010).
Longley, M.J., et al., "Mutant POLG2 Disrupts DNA Polymerase Gamma Subunits and Causes Progressive External Ophthalmoplegia," American Journal of Human Genetics 78(6):1026-1034, Cell Press, United States (Jun. 2006).
Mancuso, M., et al., "Mitochondrial DNA Depletion: Mutations in Thymidine Kinase Gene With Myopathy and SMA," Neurology 59(8):1197-1202, Lippincott Williams & Wilkins, United States (Oct. 2002).
Mancuso, M., et al., "Mitochondrial Myopathy of Childhood Associated With Mitochondrial DNA Depletion and a Homozygous Mutation (T77M) in the Tk2 Gene," Archives of Neurology 60(7):1007-1009, American Medical Association, United States (Jul. 2003).
Mandel, H., et al., "The Deoxyguanosine Kinase Gene is Mutated in Individuals With Depleted Hepatocerebral Mitochondrial DNA," Nature Genetics 29(3):337-341, Nature Pub. Co., United States (Nov. 2001).
Marti, R., et al., "Hearing Loss in a Patient With the Myopathic Form of Mitochondrial DNA Depletion Syndrome and a Novel Mutation in the TK2 Gene," Pediatric Research 68(2):151-154, Nature Publishing Group, United States (Aug. 2010).
Munro, B., et al., "Nucleoside Supplementation Modulates Mitochondrial DNA Copy Number in the Dguok –/– Zebrafish," Human Molecular Genetics 28(5):796-803, IRL Press at Oxford University Press, England (Mar. 2019).
Naviaux, R.K. and Nguyen, K.V., "POLG Mutations Associated With Alpers' Syndrome and Mitochondrial DNA Depletion," Annals of Neurology 55(5):706-712, Wiley-Liss, United States (May 2004).
Nishino, I., et al., "Thymidine Phosphorylase Gene Mutations in MNGIE, A Human Mitochondrial Disorder," Science 283(5402):689-692, American Association for the Advancement of Science, United States (Jan. 1999).
Oskoui, M., et al., "Clinical Spectrum of Mitochondrial DNA Depletion Due to Mutations in the Thymidine Kinase 2 Gene," Archives of Neurology 63(8):1122-1126, American Medical Association, United States (Aug. 2006).
Ostergaard, E., et al., "Mitochondrial Encephalomyopathy With Elevated Methylmalonic Acid is Caused by SUCLA2 Mutations," Brain: A Journal of Neurology 130(Pt 3):853-861, Oxford University Press, United Kingdom (Mar. 2007).
Paradas, C., et al., "TK2 Mutation Presenting as Indolent Myopathy," Neurology 80(5):504-506, Lippincott Williams & Wilkins, United States (Jan. 2013).
Ronchi, D., et al., "Next-Generation Sequencing Reveals DGUOK Mutations in Adult Patients With Mitochondrial DNA Multiple Deletions," Brain: A Journal of Neurology 135(Pt 11):3404-3415, Oxford University Press, United Kingdom (Nov. 2012).
Roos, S., et al., "Mitochondrial DNA Depletion in Single Fibers in a Patient With Novel TK2 Mutations," Neuromuscular Disorders 24(8):713-720, Pergamon Press, United Kingdom (Aug. 2014).
Saada, A., et al., "Mitochondrial Deoxyribonucleoside Triphosphate Pools in Thymidine Kinase 2 Deficiency," Biochemical and Biophysical Research Communications 310(3):963-966, Elsevier, United States (Oct. 2003).
Saada, A., et al., "Mutant Mitochondrial Thymidine Kinase in Mitochondrial DNA Depletion Myopathy," Nature Genetics 29(3):342-344, Nature Pub. Co., United States (Nov. 2001).
Sarzi, E., et al., "Twinkle Helicase (PEO1) Gene Mutation Causes Mitochondrial DNA Depletion," Annals of Neurology 62(6):579-587, Wiley-Liss, United States (Dec. 2007).
Spelbrink, J.N., et al., "Human Mitochondrial DNA Deletions Associated With Mutations in the Gene Encoding Twinkle, a Phage T7 Gene 4-Like Protein Localized in Mitochondria," Nature Genetics 28(3):223-231, Nature Pub. Co., United States (Jul. 2001).
Spinazzola, A., et al., "MPV17 Encodes an Inner Mitochondrial Membrane Protein and is Mutated in Infantile Hepatic Mitochondrial DNA Depletion," Nature Genetics 38(5):570-575, Nature Pub. Co., United States (May 2006).
Tulinius, M., et al., "Novel Mutations in the Thymidine Kinase 2 Gene (TK2) Associated With Fatal Mitochondrial Myopathy and Mitochondrial DNA Depletion," Neuromuscular Disorders 15(6):412-415, Pergamon Press, United Kingdom (Jun. 2005).
Tyynismaa, H., et al., "A Heterozygous Truncating Mutation in RRM2B Causes Autosomal-dominant Progressive External Ophthalmoplegia With Multiple mtDNA Deletions," American Journal of Human Genetics 85(2):290-295, Cell Press, United States (Aug. 2009).
Tyynismaa, H., et al., "Thymidine Kinase 2 Mutations in Autosomal Recessive Progressive External Ophthalmoplegia With Multiple Mitochondrial DNA Deletions," Human Molecular Genetics 21(1):66-75, IRL Press at Oxford University Press, United Kingdom (Jan. 2012).
Vila, M.R., et al., "Reversion of mtDNA Depletion in a Patient With TK2 Deficiency," Neurology 60(7):1203-1205, Lippincott Williams & Wilkins, United States (Apr. 2003).
Wang, J., et al., "TK2-Related Mitochondrial DNA Maintenance Defect, Myopathic Form," GeneReviews®, accessed at URL:https://www.ncbi.nlm.nih.gov/books/NBK114628/ on Sep. 20, 2022, National Library of Medicine, United States (Dec. 6, 2012).
Wang, L., et al., "Molecular Insight Into Mitochondrial DNA Depletion Syndrome in Two Patients With Novel Mutations in the

(56) References Cited

OTHER PUBLICATIONS

Deoxyguanosine Kinase and Thymidine Kinase 2 Genes," Molecular Genetics and Metabolism 84(1):75-82, Academic Press, United States (Jan. 2005).

Cano-Soldado, P., et al., "Transporters That Translocate Nucleosides and Structural Similar Drugs: Structural Requirements for Substrate Recognition," Med. Res. Rev. 32(2): 428-457, 429 Wiley Periodicals, Untied States (2011).

Zhou X.J,, et al., "Absence of Food Effect on the Pharmacokinetics of Telbivudine Following Oral Administration in Healthy Subjects," J. Clin. Pharmacol. 46(3):275-81, American College of Clinical Pharmacology, United States (2006).

PRODRUGS OF DEOXYNUCLEOSIDES FOR TREATMENT OF DISEASES CAUSED BY UNBALANCED NUCLEOTIDE POOLS

CROSS REFERENCE TO RELATED APPLICATION

The present This application is a continuation of U.S. application Ser. No. 17/046,865, filed Oct. 12, 2020, which is a national phase application under 35 U.S.C. § 371 of International Appl. No. PCT/US2019/027364, filed Apr. 2, 2019, which claims priority to U.S. Provisional Patent Application No. 62/656,861, filed Apr. 12, 2018, each of which is incorporated herein by reference in their entireties.

FIELD OF THE INVENTION

The present invention relates generally to prodrugs for delivering deoxynucelosides and uses of the same in treating diseases caused by unbalanced nucleotide pools, including mitochondrial DNA depletion syndromes.

BACKGROUND OF THE INVENTION

Mitochondrial diseases are clinically heterogeneous diseases due to defects of the mitochondrial respiratory chain (RC) and oxidative phosphorylation, the biochemical pathways that convert energy in electrons into adenosine triphosphate (ATP). The respiratory chain is comprised of four multi-subunit enzymes (complexes I-IV) that transfer electrons to generate a proton gradient across the inner membrane of mitochondria and the flow of protons through complex V drives ATP synthesis (DiMauro and Schon 2003; DiMauro and Hirano 2005). Coenzyme Qio (CoQio) is an essential molecule that shuttles electrons from complexes I and II to complex III. The respiratory chain is unique in eukaryotic, e.g., mammalian, cells by virtue of being controlled by two genomes, mitochondrial DNA (mtDNA) and nuclear DNA (nDNA). As a consequence, mutations in either genome can cause mitochondrial diseases. Most mitochondrial diseases affect multiple body organs and are typically fatal in childhood or early adult life. There are no proven effective treatments for mitochondrial diseases, only supportive therapies, such as the administration of CoQio and its analogs to enhance respiratory chain activity and to detoxify reactive oxygen species (ROS) that are toxic by-products of dysfunctional respiratory chain enzymes.

Mitochondrial DNA depletion syndrome (MDS), which is a subgroup of mitochondrial disease, is a frequent cause of severe childhood encephalomyopathy characterized molecularly by reduction of mitochondrial DNA (mtDNA) copy number in tissues and insufficient synthesis of mitochondrial RC complexes (Hirano, et al. 2001). Mutations in several nuclear genes have been identified as causes of infantile MDS, including: TK2, DGUOK, POLG, POLG2, SCLA25A4, MPV17, RRM2B, SUCLA2, SUCLG1, TYMP, OPA1, and ClOorfl (PEO1). (Bourdon, et al. 2007; Copeland 2008; Elpeleg, et al. 2005; Mandel, et al. 2001; Naviaux and Nguyen 2004; Ostergaard, et al. 2007; Saada, et al. 2003; Sarzi, et al. 2007; Spinazzola, et al, 2006). In addition, mutations in these nuclear genes can also cause multiple deletions of mtDNA with or without mtDNA depletion (Behin, et al. 2012; Garone, et al. 2012; Longley, et al. 2006; Nishino, et al. 1999; Paradas, et al. 2012; Ronchi, et al. 2012; Spelbrink, et al. 2001; Tyynismaa, et al. 2009; Tyynismaa, et al. 2012; Van Goethem, et al. 2001).

One of these genes is TK2, which encodes thymidine kinase (TK2), a mitochondrial enzyme required for the phosphorylation of the pyrimidine nucleosides (thymidine and deoxycytidine) to generate deoxythymidine monophosphate (dTMP) and deoxycytidine monophosphate (dCMP) (Saada, et al. 2001). Mutations in TK2 impair the mitochondrial nucleoside/nucleotide salvage pathways required for synthesis of deoxynucleotide triphosphate (dNTP), the building blocks for mDNA replication and repair.

TK2 deficiency was first described in 2001 by Saada and colleagues (Saada, et al. 2001), in four affected children originating from four different families, who suffered from severe, devastating myopathy. After an uneventful early development, at ages 6-36 months the patients developed hyperCKemia, severe muscle hypotonia with subsequent loss of spontaneous activity. The disease was rapidly progressive and two patients were mechanically ventilated at 3 years, while two other patients were already dead by the time of the report.

After the first description, sixty additional patients have been reported in literature and at least twenty-six further patients have been diagnosed but not reported (Alston, et al. 2013; Bartesaghi, et al. 2010: Behin, et al. 2012; Blakely, et al. 2008: Carrozzo, et al. 2003; Chanprasert, et al. 2013; Collins, et al 2009; Galbiati, et al. 2006; Gotz, et al. 2008; Leshinsky-Silver, et al, 2008; Lesko, et al. 2010: Mancuso, et al. 2002; Mancuso, et al. 2003; Marti, et al. 2010; Oskoui, et al. 2006; Paradas, et al. 2012; Roos, et al. 2014; Tulinius, et al. 2005; Tyynismaa, et. al. 2012; Vila, 2003; Wang, et al. 2005), resulting in ninety patients, 53 males and 37 females. The twenty-six patients recently diagnosed were identified through next-generation DNA sequencing. This large number of newly identified cases suggests that TK2 deficiency is an under diagnosed disorder.

TK2 deficiency manifests a wide clinical and molecular genetic spectrum with the majority of patients manifesting in early childhood with a devastating clinical course, while others have slowly progressive weakness over decades.

Treatment for TK2 deficiency, like most MDS and mitochondrial disorders, has been limited to supportive therapies. Administration of deoxythymidine monophosphate (dTMP) and deoxycytidine monophosphate (dCMP) has been shown to improve the conditions of both TK2 knock-in mutant mice and human patients with TK2 deficiency (U.S. application Ser. No. 15/082,207, which is incorporated herein in its entirety), as has administration of the deoxynucleosides (e.g. deoxythymidine (dT) or deoxycytidine (dC) or mixtures thereof) (WO2016205671, also incorporated herein in its entirety). However, there remains a need for additional therapeutic interventions for TK2 deficiency.

Additionally, there is a need for treatment for other forms of MDS and other diseases characterized by unbalanced nucleotide pools. For example, several mendelian disorders with mtDNA depletion or multiple deletions, or both are characterized by unbalanced deoxynucleotide triphosphate pools that lead to defects of mtDNA replication. One such disorder, DGUOK mutations impair the intramitochondrial enzyme deoxy guanosine kinase, which normally phosphorylates the deoxypurine nucleosides deoxguanosine and deoxycytidine to generate deoxguanosine monophosphate (dGMP) and deoxycytidine monophosphate (dCMP). Other nuclear genes that disrupt mitochondrial dNTP pools include TYMP, RRM2B, SUCLA2, SUCLG1 and MPV17. Therapies that restore dNTP pool balance would be useful to treat these disorders as well.

SUMMARY OF THE INVENTION

The present invention relates generally to prodrugs for delivering deoxynucleosides.

In one aspect, the present invention provides compounds of Formula I:

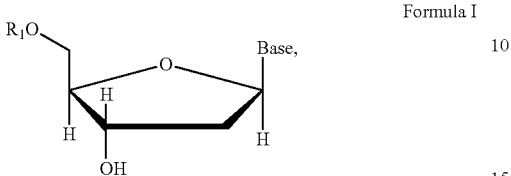

Formula I wherein Base refers to an optionally substituted heterocyclic base or an optionally substituted heterocyclic base with a protected amino group;
$R^1$ is selected from the group consisting of optionally substituted acyl, optionally substituted 0-linked amino acid,

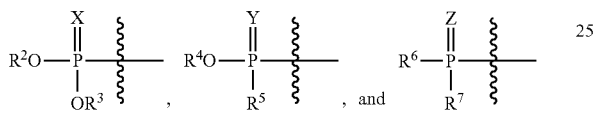

X, Y and Z are each independently selected from O and S;
$R^2$, $R^3$ and $R^4$ are each independently selected from hydrogen, optionally substituted $C_{1-24}$ alkyl, optionally substituted $C_{2-24}$ alkenyl, optionally substituted $C_{2-24}$ alkynyl, optionally substituted $C_{3-6}$ cycloalkyl, optionally substituted $C_{3-6}$ cycloalkenyl, optionally substituted aryl, optionally substituted heteroaryl, optionally substituted aryl($C_{1-6}$)alkyl,

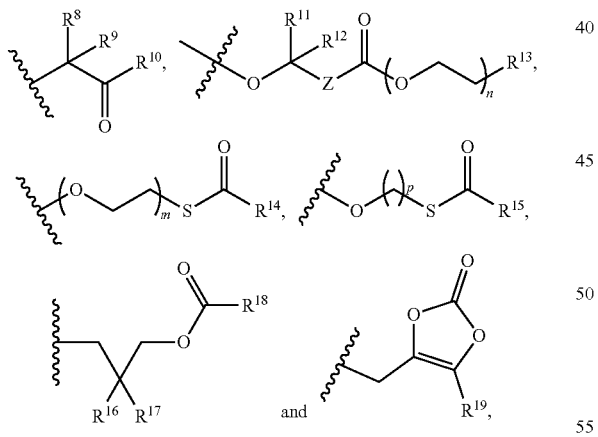

or $R^2$ and $R^3$ can be taken together to form a cyclic moiety;
$R^5$, $R^6$ and $R^7$ are each independently selected from optionally substituted $C_{1-24}$ alkyl, optionally substituted $C_{2-24}$ alkenyl, optionally substituted $C_{2-24}$ alkynyl, optionally substituted $C_{3-6}$ cycloalkyl, optionally substituted $C_{3-6}$ cycloalkenyl, $NR^{20}R^{21}$, optionally substituted N-linked amino acid, optionally substituted N-linked amino acid ester;
$R^8$, $R^9$, $R^{11}$ and $R^{12}$ are each independently selected from hydrogen, optionally substituted C1-24 alkyl and optionally substituted aryl;

$R^{10}$ and $R^{13}$ are each independently selected from hydrogen, optionally substituted C1-24 alkyl and optionally substituted aryl, an optionally substituted —O—C1-24 alkyl, an optionally substituted —O-aryl, an optionally substituted —O-heteroaryl, an optionally substituted —O-monocyclic hetercyclyl;

$R^{14}$, $R^{15}$ and $R^{19}$ are each independently selected from hydrogen, an optionally substituted $C_{1-24}$ alkyl and an optionally substituted aryl;

$R^{16}$ and $R^{17}$ are each independently selected from —CN, optionally substituted $C_{2-8}$ organylcarbonyl, $C_{2-8}$ alkoxycarbonyl and $C_{2-8}$ organylaminocarbonyl;

$R^{18}$ is selected from hydrogen, optionally substituted $C_{1-24}$ alkyl, optionally substituted $C_{2-24}$ alkenyl, optionally substituted $C_{2-24}$ alkynyl; optionally substituted $C_{3-6}$ cycloalkyl and optionally substituted $C_{3-6}$ cycloakenyl;

$R^{20}$ and $R^{21}$ are each independently selected from hydrogen, optionally substituted $C_{1-24}$ alkyl, optionally substituted $C_{2-24}$ alkenyl, optionally substituted $C_{2-24}$ alkynyl; optionally substituted $C_{3-6}$ cycloalkyl and optionally substituted $C_{3-6}$ cycloalkenyl; and n, m and p are each independently selected from 0, 1, 2, or 3.

In another aspect, the prodrugs are compounds of Formula II:

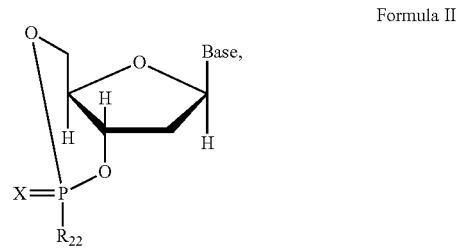

Formula II wherein Base refers to an optionally substituted heterocyclic base or an optionally substituted heterocyclic base with a protected amino group;
X is selected from S and O; and
$R^{22}$ is selected from —O⁻, —OH, —O-alkyl, optionally substituted $C_{1-6}$ alkoxy,

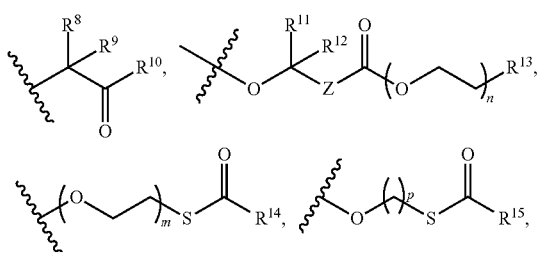

optionally substituted N-linked amino acid and optionally substituted N-linked amino acid ester;
wherein $R^8$, $R^9$, $R^{10}$$R^{11}$, $R^{12}$, $R^{13}$, $R^{14}$, $R^{14}$, $R^{15}$, n, m and p are defined as above.

In still another aspect, the prodrugs are compounds of Formula III:

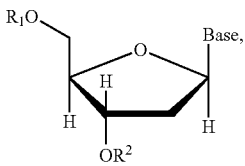

Formula III wherein Base refers to an optionally substituted heterocyclic base or an optionally substituted heterocyclic base with a protected amino group;

$R^1$ and $R^2$ are independent selected from hydrogen, phosphate (including mono-, di-, or tri-phosphate and the modified phosphates of Formula I); straight chained, branced or cyclic alkyl; acyl; CO-alkyl, CO-alkoxyalkyl; CO-aryloxyalkyl; CO-substituted aryl, sulfonate ester; alkylsulfonyl; arylsulfonyl; aralkylsulfonyl; a lipid; a phospholipid; an amino acid; a carbohydrate; a peptide and cholesterol.

In yet another aspect, the present invention also generally relates to methods of treating a disease or disorder characterized by unbalanced nucleotide pools in a subject in need thereof comprising administering to the subject a therapeutically effective amount of at least one prodrug of the present invention. The prodrug can be administered as such (i.e. alone) or in the form of a pharmaceutical composition.

Suitable diseases or disorders include, but are not limited to, consisting of TK2 deficiency, RRM2B deficiency, mutations in TYMP, SUCLA2 deficiency, SUCLG1 deficiency, MPV17 deficiency and DGUOK mutations.

Administration can be via any route including, but not limited to, intrathecal, parental, mucosal and transdermal.

The amount of the at least one prodrug or composition comprising the same administered can be from about 25 mg/kg/day to about 1,000 mg/kg/day.

DETAILED DESCRIPTION OF THE INVENTION

I. Definitions

As used herein, "subject" refers to mammals. Mammals include canines, felines, rodents, bovine, equines, porcines, ovines, and primates. Thus, the invention can be used in veterinary medicine, e.g., to treat companion animals, farm animals, laboratory animals in zoological parks, and animals in the wild. The invention is particularly desirable for human medical applications As used herein, "patient" refers to a human subject. In some embodiments of the present invention, the "patient" is known or suspected of having a disease or disorder characterized by unbalanced nucleotide pools, mitochondrial disease, mitochondrial DNA depletion syndrome, or TK2 deficiency.

As used herein, "therapeutically effective amount" refers to an amount sufficient to cause an improvement in a clinically significant condition in the subject, or delays or minimizes or mitigates one or more symptoms associated with the disease or disorder, or results in a desired beneficial change of physiology in the subject.

As used herein, "treat", "treatment", and the like refer to a means to slow down, relieve, ameliorate or alleviate at least one of the symptoms of the disease or disorder, or reverse the disease or disorder after its onset.

As used herein, "prevent", "prevention", and the like refer to acting prior to overt disease or disorder onset, to prevent the disease or disorder from developing or minimize the extent of the disease or disorder, or slow its course of development.

As used herein, "in need thereof" refers to a subject known or suspected of having or being at risk of having a disease or disorder characterized by unbalanced nucleotide pools, mitochondrial disease, mitochondrial DNA depletion syndrome, or TK2 deficiency.

As used herein, "prodrug" refers to a derivative of the deoxynucleoside that undergoes a transformation under the conditions of use, such as within the body, to release the deoxynucleoside. Prodrugs are frequently, but not necessarily, pharmacologically inactive until converted into the active form. Prodrugs can be obtained by bonding a promoiety, typically via a functional group, to a drug.

As used herein, "promoiety" refers to a group bonded to the deoxynucleoside, typically to a functional group, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously.

As used herein, "an adverse effect" is an unwanted reaction caused by the administration of a drug. In most cases, the administration of the deoxynucleosides caused no adverse effects. The most expected adverse effect would be a minor gastrointestinal intolerance.

As used herein, "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl (alkyl), heterocyclyl(alkyl), hydroxy, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, azido, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "Ca to Cb" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heterocyclyl can contain from "a" to "b", inclusive, carbon atoms. Thus, for example, a "C1 to C4 alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "C1-C4 alkyl" or similar designations. By way of example only, "C1-C4 alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a C6-C14 aryl group, a C6-C10 aryl group, or a C6 aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2, 3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsub stituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl).

As used herein, "aralkyl" and "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaralkyl" and "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

As used herein, "alkoxy" refers to the formula —OR wherein R is an alkyl, an alkenyl, an alkynyl, a cycloalkyl, a cycloalkenyl, aryl, heteroaryl, heteroalicyclyl, aralkyl, heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heteroalicyclyl, aralkyl, heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4,N^4$-ethanocytosin, $N^6,N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

As used herein, "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. N-linked amino acids can be substituted or unsubstituted.

As used herein, "—N-linked amino acid ester" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)—, and naphthyl-O—C(=O)—. N-linked amino acid ester derivatives can be substituted or unsubstituted.

As used herein, "—O-linked amino acid" refers to an amino acid that is attached to the indicated moiety via the hydroxy from its main-chain carboxylic acid group. When the amino acid is attached in an —O-linked amino acid, the hydrogen that is part of the hydroxy from its main-chain carboxylic acid group is not present and the amino acid is attached via the oxygen. O-linked amino acids can be substituted or unsubstituted.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

The term "amino acid" includes naturally occuning and synthetic, βγ or δ amino acids, The amino acid can be in the D- or L-configuration. The amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

The term "deoxynucleoside", as used herein, refers to any nucleoside containing a deoxy sugar, i.e., any compound formally derived from a sugar by replacing a hydroxy group by a hydrogen atom, e.g., deoxyribose.

The term "dNTP", as used herein, refers to deoxyribonucleotide triphosphate. Each dNTP is made up of a phosphate group, a deoxyribose sugar and a nitrogenous base. There are four different dNTPs and can be split into two groups: the purines and the pyrimidines. dATP, (deoxyadenosine 5'-triphosphate), and dGTP, (deoxyguanine 5'-triphosphate), make up the purines, while dTTP, (deoxythymidine 5'-triphosphate), and dCTP, (deoxycytidine 5'-triphosphate), make up the pyrimidines. Adenine and guanine, the bases which feature in the purines, both have a double ring structure, while thymine and cytosine, the bases which feature in the purines, both have a single ring structure.

The term "mitochondrial DNA depletion syndrome", as used herein, refers to a class of phenotypically diverse diseases and disorders characterized by a severe reduction in mitochondrial DNA (mtDNA) content in affected tissues and organs, for example, muscle, liver brain and/or GI tract. The reduction or depletion can result from any imbalance in the mitochondrial nucleotide pool available for mtDNA replication, as well as abnormalities in mitochondrial replication. Based on age at onset, two subtypes are distinguished: congenital (or early-onset) and infantile (or later-onset). Although survival is longer in the later-onset form, the syndrome is fatal in almost all patients, and currently there is no effective treatment.

I. Prodrugs

The present invention provides deoxynucleotide prodrugs. "Deoxynucleoside" refers to 2'-deoxynucleosides, e.g. deoxycytidine (dC, shown below), deoxythymidine (dT) deoxyadenosine (dA) and deoxyguanosine (dG). The full length name and common abbreviation for each will be used interchangeably.

In particular embodiments, Base is selected from cytosine, thymine, guanine and adenine.

As such, the prodrugs describe herein are deoxycytidine prodrugs (dC prodrugs), deoxythymidine prodrugs (dT prodrugs), deoxyguanosine prodrugs (dG prodrugs) and deoxyadenosine prodrugs (dA prodrugs).

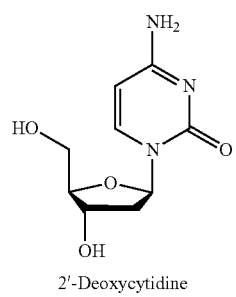

2'-Deoxycytidine

The prodrugs are preferably in the natural, β-D-configuration.

In one embodiment, the prodrug strategy involves masking the reactive groups, e.g. the charged —OH and phosphate groups in vivo, to permit passage across cell membranes.

In one embodiment, the present invention provides prodrugs of Formula I:

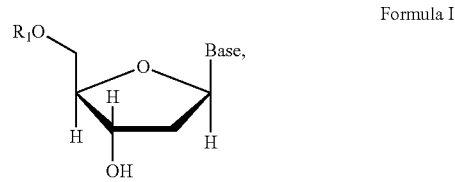

Formula I wherein Base refers to an optionally substituted heterocyclic base or an optionally substituted heterocyclic base with a protected amino group;

$R^1$ is selected from the group consisting of optionally substituted acyl, optionally substituted O-linked amino acid,

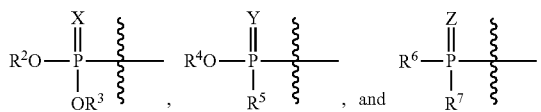

X, Y and Z are each independently selected from O and S;

$R^2$, $R^3$ and $R^4$ are each independently selected from hydrogen, optionally substituted $C_{1-24}$ alkyl, optionally substituted $C_{2-24}$ alkenyl, optionally substituted $C_{2-24}$ alkynyl, optionally substituted $C_{3-6}$ cycloalkyl, optionally substituted $C_{3-6}$ cycloalkenyl, optionally substituted aryl, optionally substituted heteroaryl, optionally substituted aryl($C_{1-6}$) alkyl,

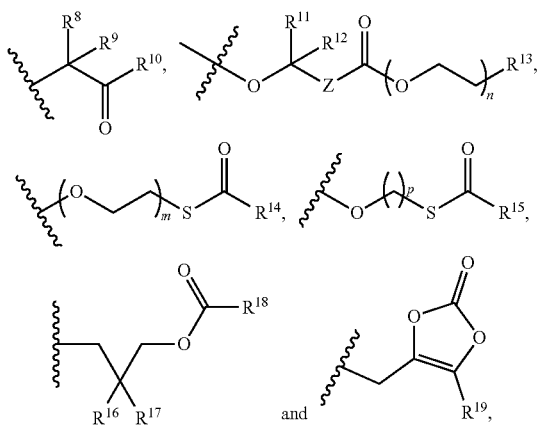

or $R^2$ and $R^3$ can be taken together to form a cyclic moiety;

$R^5$, $R^6$ and $R^7$ are each independently selected from optionally substituted $C_{1-24}$ alkyl, optionally substituted $C_{2-24}$ alkenyl, optionally substituted $C_{2-24}$ alkynyl, optionally substituted $C_{3-6}$ cycloalkyl, optionally substituted $C_{3-6}$ cycloalkenyl, $NR^{20}R^{21}$, optionally substituted N-linked amino acid, optionally substituted N-linked amino acid ester;

$R^8$, $R^9$, $R^{11}$ and $R^{12}$ are each independently selected from hydrogen, optionally substituted C1-24 alkyl and optionally substituted aryl;

$R^{10}$ and $R^{13}$ are each independently selected from hydrogen, optionally substituted C1-24 alkyl and optionally substituted aryl, an optionally substituted —O—C1-24 alkyl, an optionally substituted —O-aryl, an optionally substituted —O-heteroaryl, an optionally substituted —O-monocyclic hetercyclyl;

$R^{14}$, $R^{15}$ and $R^{19}$ are each independently selected from hydrogen, an optionally substituted $C_{1-24}$ alkyl and an optionally substituted aryl;

$R^{16}$ and $R^{17}$ are each independently selected from —CN, optionally substituted $C_{2-8}$ organylcarbonyl, $C_{2-8}$ alkoxycarbonyl and $C_{2-8}$ organylaminocarbonyl;

$R^{18}$ is selected from hydrogen, optionally substituted $C_{1-24}$ alkyl, optionally substituted $C_{2-24}$ alkenyl, optionally substituted $C_{2-24}$ alkynyl; optionally substituted $C_{3-6}$ cycloalkyl and optionally substituted $C_{3-6}$ cycloakenyl;

$R^{20}$ and $R^{21}$ are each independently selected from hydrogen, optionally substituted $C_{1-24}$ alkyl, optionally substituted $C_{2-24}$ alkenyl, optionally substituted $C_{2-24}$ alkynyl; optionally substituted $C_{3-6}$ cycloalkyl and optionally substituted $C_{3-6}$ cycloakenyl; and n, m and p are each independently selected from 0, 1, 2, or 3.

In a particular embodiment, the prodrug is a compound of Formula Ia:

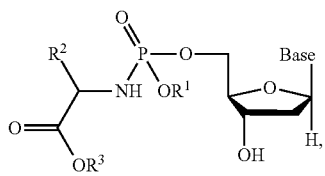

Formula Ia wherein each of $R^1$, $R^2$ and $R^3$ are independently selected from hydrogen, optionally substituted $C_{1-24}$ alkyl, optionally substituted $C_{2-24}$ alkenyl, optionally substituted $C_{2-24}$ alkynyl, optionally substituted $C_{3-6}$ cycloalkyl, optionally substituted $C_{3-6}$ cycloalkenyl, optionally substituted aryl, optionally substituted heteroaryl and optionally substituted aryl($C_{1-6}$) alkyl.

In a particular embodiment, $R^1$ is aryl, $R^2$ is $C_{1-24}$ alkyl and $R^3$ is $C_{1-24}$ alkyl.

In another particular embodiment, $R^2$ is an amino acid side chain.

In a further particular embodiment, the prodrug is selected from one of the following compounds:

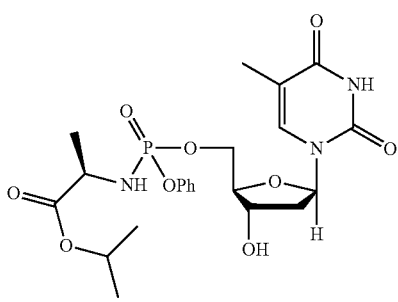

1

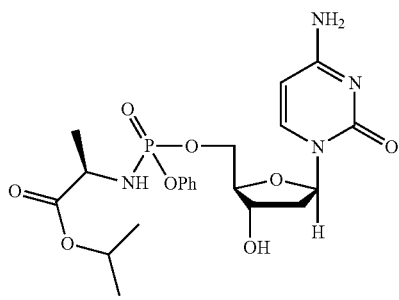

2

In another embodiment, the present invention provides prodrugs of Formula II:

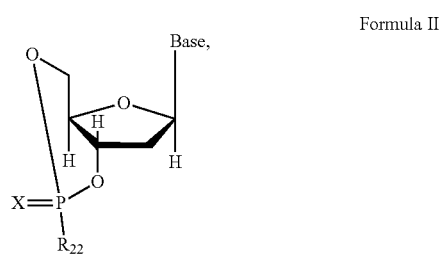

Formula II wherein Base refers to an optionally substituted heterocyclic base or an optionally substituted heterocyclic base with a protected amino group;

X is selected from S and O; and $R^{22}$ is selected from —O⁻, —OH, —O-alkyl, optionally substituted $C_{1-6}$ alkoxy,

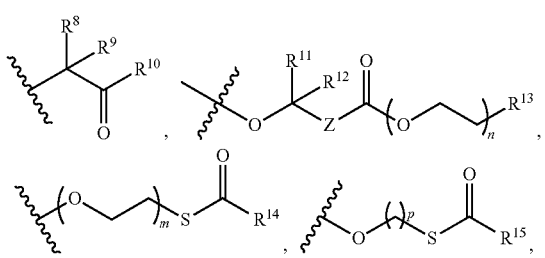

optionally substituted N-linked amino acid and optionally substituted N-linked amino acid ester;

wherein $R^8$, $R^9$, $R^{10}$, $R^{11}$, $R^{12}$, $R^{13}$, $R^{14}$, $R^{15}$, n, m and p are defined as above.

In a particular embodiment, the prodrug is a compound of Formula IIa:

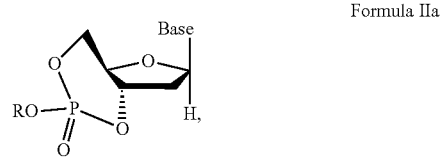

Formula IIa wherein R is $C_{1-4}$ alkyl.

In a still further particular embodiment, the prodrug is selected from one of the following compounds:

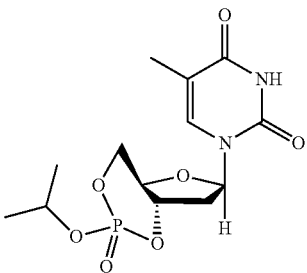

3

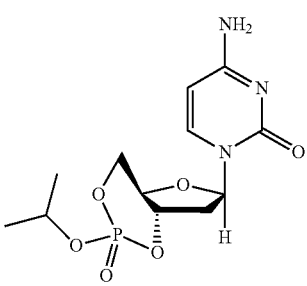

4

In still another embodiment, the present invention provides prodrugs of Formula III:

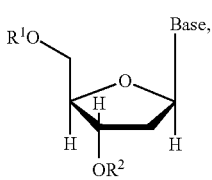

Formula III wherein Base refers to an optionally substituted heterocyclic base or an optionally substituted heterocyclic base with a protected amino group;

$R^1$ and $R^2$ are independent selected from hydrogen, phosphate (including mono-, di-, or tri-phosphate and the modified phosphates of Formula I); straight chained, branced or cyclic alkyl; optionally substituted acyl; CO-alkyl, CO-alkoxyalkyl; CO-aryloxyalkyl; CO-substituted aryl, sulfonate ester; alkylsulfonyl; arylsulfonyl; aralkylsulfonyl; a lipid; a phospholipid; an amino acid; a carbohydrate; a peptide and cholesterol.

In one embodiment, $R^2$ is an amino acid, i.e. the compound for Formula III is a 3'-amino acid ester, e.g. a compound of Formula IIIa:

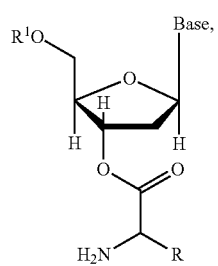

Formula IIIa wherein R is the side chain of the amino acid.

In a particular embodiment the amino acid is valine (i.e. R is $CH(CH_3)_2$).

In a more particular embodiment, the prodrug is a compound of Formula IIIb:

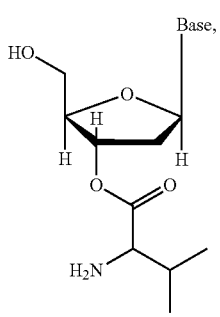

Formula IIIb wherein Base refers to an optionally substituted heterocyclic base or an optionally substituted heterocyclic base with a protected amino group.

In a still more particular embodiment, the prodrug is selected from one of the following compounds:

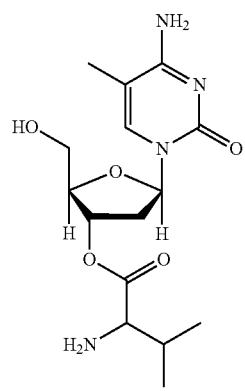

5

6

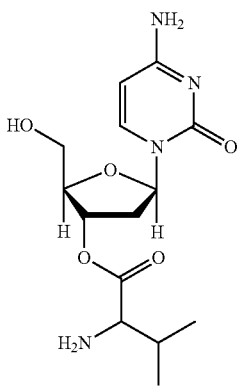

In a still further particular embodiment, the prodrug is selected from one of the following compounds:

7

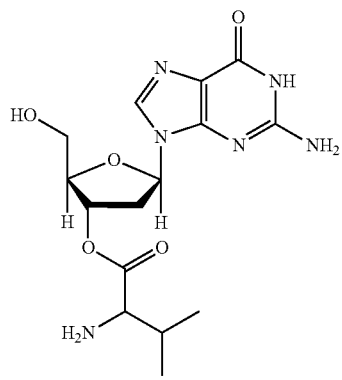

8

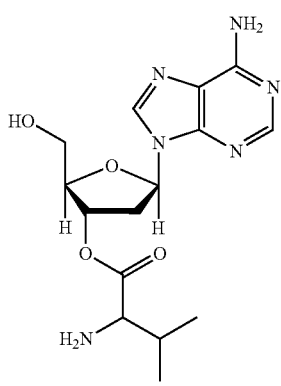

In a still further embodiment, the prodrug is a compound of Formula IIIc:

Formula IIIc

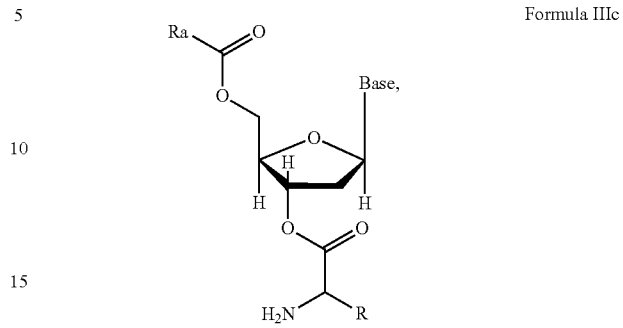

wherein Base refers to an optionally substituted heterocyclic base or an optionally substituted heterocyclic base with a protected amino group;

Ra is straight-chained, branched or cyclic alkyl and R is a side chain of an amino acid.

In a particular embodiment, Ra is selected from methyl, ethyl, n-propyl, isopropyl, n-butyl, sec-butyl, isobutyl and tert-butyl and R is $CH(CH_3)_2$.

II. Methods of Use

The present invention provides a method of treating a disease or disorder characterized by unbalanced nucleotide pools in a subject in need thereof comprising administering to the subject a therapeutically effective amount of at least one prodrug described herein.

In one embodiment, prodrugs described hereinabove can be utilized in the present method.

The prodrug can be administered as such (i.e. alone) or in the form of a pharmaceutical composition. Pharmaceutical compositions comprising one of more prodrugs for administration may comprise a therapeutically effective amount of the prodrug and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

In a particular embodiment, the disclosed method can be used to treat a mitochondrial DNA (mtDNA) depletion syndrome (MDS). Each nucleated cell contains several hundreds of mitochondria, which are unique organelles in being under dual genome control. The mitochondria contain their own DNA, the mtDNA, but most of mitochondrial proteins are encoded by nuclear genes, including all the proteins required for replication, transcription, and repair of mtDNA.

The maintenance of mtDNA requires proteins essential for mtDNA synthesis, for maintenance of the mitochondrial nucleotide pool, and for mediating mitochondrial fusion. The enzymes that synthesize mtDNA require a balanced supply of intramitochondrial nucleotides. These are supplied through mitochondrial nucleotide salvage pathways and the import of nucleotides from the cytosol via specific transporters. To function properly in mtDNA synthesis the quantities of these enzymes need to be balanced appropriately. The proteins known to be required for mtDNA synthesis are encoded by nuclear genes. When pathogenic variants disrupt the function of any one of the proteins encoded by these genes, mtDNA synthesis is impaired, resulting in either quantitative defects in mtDNA (mtDNA depletion) or qualitative defects in mtDNA (multiple mtDNA deletions). To date, pathogenic variants in more than 20 nuclear genes are known to be associated with mtDNA maintenance defects.

In one embodiment, the mt DNA depletion syndrome is a nuclear DNA-based mtDNA depletion syndrome. In a particular embodiment, the nuclear DNA encodes a protein involved in nucleotide metabolism. Imbalance in free nucleotide concentrations leads to disturbances in mtDNA replication and in consequence to mtDNA copy number decrease.

In a particular embodiment, the method of the present invention is useful in treating a disease or disorder caused by a deoxyribonucleoside triphosphate (dNTP) pool imbalance. dTNPs are the precursors used by DNA polymerases for replication and repair of nuclear and mitochondrial DNA in animal cells. The concentration of dNTPs depends on a balance between synthesis, consumption and degradation.

Accurate DNA synthesis requires adequate amounts of each dNTP and appropriately balanced dNTP pools. Total cellular pool sizes are in the range of 10-100 pmoles of each dNTP/million cells during S phase, with mitochondrial pools representing at most 10% of the total. In quiescent or differentiated cells pools are about 10-fold lower both in the cytosol and mitochondria. Contrary to what may be expected on the basis of the roughly equimolar abundance of the 4 nitrogen bases in DNA, the four dNTPs are present in the pools in different ratios, with pyrimidines often exceeding purines. Individual cell lines may exhibit different pool compositions even if they are derived from the same animal species. An increase in the concentration of one dNTP usually results in depletion of another dNTP.

The mtDNA depletion syndrome may involve a particular tissue or organ, e.g., the muscle, the liver, the brain and/or the GI tract. In a particular embodiment, the mtDNA depletion syndrome is a myopathic or hepato-cerebral syndrome.

Exemplary disorders characterized by unbalanced nucleotide pools include, but are not limited to, TK2 deficiency, deficiencies related to RRM2B (encoding p53R2, the p53 inducible small subunit of ribonucleotide reductase, RNR) and mutations in TYMP (encoding thymidine phosphorylase, TP) which cause mitochondrial neurogastrointestinal encephalomyopathy (MNGIE). Additional nuclear genes that disrupt mitochondrial dNTP pools include but are not limited to SUCLA2, SUCLG1 and MPV17. A parallel defect of deoxyguanosine kinase (dGK), due to autosomal recessive mutations in DGUOK with deficiencies in dGMP and dAMP, causes mtDNA depletion typically manifesting as early childhood-onset hepatocerebral disease (Mandel, et al. 2001). Disorders related to these genes can also be treated with the methods herein.

In a particular embodiment, the disorder is thymidine kinase 2 (TK2) deficiency. TK2 is a mitochondrial enzyme participating in the salvage of deoxyribonucleotides needed for mitochondrial DNA (mtDNA) replication. TK2 catalyzes the first and rate-limiting step of the deoxypyrimidine salvage pathway. Autosomal recessive TK2 mutations cause a spectrum of disease from infantile onset to adult onset manifesting primarily as myopathy.

As the mechanisms of other forms of MDS and other disorders become elucidated, the proper deoxynucleoside(s) for treatment can be determined by the skilled practitioner.

For example, for patients with TK2 deficiency, administration of prodrugs of dC and/or dT would be administered. In another example, for patients with DGUOK deficiencies, administration of prodrugs of dG and/or dA would be administered.

In one embodiment, the present method further includes identifying patients with a disease or disorder characterized by unbalanced nucleotide pools. In one embodiment, that disease or disorder is TK2 deficiency. Patients that exhibit the phenotype discussed above for TK2 deficiency including the most typical presentation of progressive muscle disease characterized by generalized hypotonia, proximal muscle weakness, loss of previously acquired motor skills, poor feeding, and respiratory difficulties, can be tested to definitively diagnose the disease.

Molecular genetic testing using a panel of genes known to cause mtDNA depletion syndrome should be performed (Chanprasert, et al. 2012) can also be used to identify patients with a disease or disorder characterized by unbalanced nucleotide pools.

The TK2 gene is the only gene in which mutations are known to cause TK2-related mitochondrial DNA depletion syndrome. This testing can include a sequence analysis of the entire coding and exon/intron junction regions of TK2 for sequence variants and deletion/duplication. If compound heterozygous or homozygous deleterious mutations are identified in the sequence analysis, the diagnosis of TK2 deficiency is confirmed, and thus, the subject would benefit from the deoxynucleoside therapy. If sequence analysis does not identify two compound heterozygous or homozygous deleterious mutations, deletion/duplication analysis should be considered to determine and/or confirm a TK2 deficiency diagnosis.

Further tests to determine and/or confirm a TK2 deficiency diagnosis may include testing serum creatine kinase (CK) concentration, electromyography, histopathology on skeletal muscle, mitochondrial DNA (mtDNA) content (copy number), and electron transport chain (ETC) activity in skeletal muscle. If one or more of the following is found in these tests, the TK2 deficiency is determined and/or confirmed. Elevated CK concentration as compared to healthy controls can indicate TK2 deficiency. A skeletal muscle biopsy can be performed, and then a mtDNA content analysis in skeletal muscle performed. If the skeletal muscle biopsy shows prominent variance in fiber size, variable sarcoplasmic vacuoles, variable increased connective tissue, and ragged red fibers as well as increased succinate dehydrogenase (SDH) activity and low to absent cytochrome c oxidase (COX) activity, and mtDNA copy number is severely reduced (typically less than 20% of age- and tissue-matched healthy controls), a diagnosis of TK2 deficiency can be determined and/or confirmed (Chanprasert, et al. 2012).

Additionally, TK2 deficiency is inherited in an autosomal recessive manner. Thus, a sibling of an affected patient can be tested as early as possible after birth to diagnose the disease.

Administration can be via any route including, but not limited to, intrathecal, parental, mucosal and transdermal.

In one embodiment, administration is oral. Exemplary oral dosage forms include, but are not limited to, capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semi-solid, or liquid polyols. Solutions and syrups may comprise water, polyols, and sugars. The prodrugs described herein can be added to any form of liquid a patient would consume including but not limited to, milk, both cow's and human breast, infant formula, and water. The prodrug may be coated with or admixed with a material that delays disintegration and/or absorption in the gastrointestinal tract. Thus, the sustained release may be achieved over many hours.

In another embodiment, administration is intrathecal. Intrathecal administration involves injection of the drug into the spinal canal, more specifically the subarachnoid space such that it reaches the cerebrospinal fluid. This method is commonly used for spinal anesthesia, chemotherapy, and pain medication. Intrathecal administration can be performed by lumbar puncture (bolus injection) or by a port-catheter system (bolus or infusion). The catheter is most commonly inserted between the laminae of the lumbar vertebrae and the tip is threaded up the thecal space to the desired level (generally L3-L4). Intrathecal formulations most commonly use water, and saline as excipients but EDTA and lipids have been used as well.

In yet another embodiment, administration is parenteral, including intravenous. Pharmaceutical compositions adapted for parenteral administration include aqueous and non-aqueous sterile injectable solutions or suspensions, which may contain anti-oxidants, buffers, bacteriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate. Additionally, since some patients may be receiving enteral nutrition by the time treatment begins, the prodrug(s) can be administered through a gastronomy feeding tube or other enteral nutrition means.

Pharmaceutical compositions adapted for nasal and pulmonary administration may comprise solid carriers such as powders, which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for transdermal administration may be provided as discrete patches intended to remain in intimate contact with the epidermis of the recipient over a prolonged period of time.

The amount of the at least one prodrug or composition comprising the same administered can be from about 25 mg/kg/day to about 1,000 mg/kg/day. A further preferred dose ranges from about 200 mg/kg/day to about 800 mg/kg day. A further preferred dose ranges from about 100 mg/kg/day to about 600 mg/kg/day, such as, for example, from about 250 mg/kg/day to about 500 mg/kg/day, from about 300 mg/kg/day to about 500 mg/kg/day or from about 400 mg/kg/day to about 500 mg/kg/day.

In one embodiment, the dose is from about 20% equimolar to about 100% equimolar to the canonical nucleoside (dT, dC, dG, dA), e.g. from about 20% to about 80%, from about 20% to about 50%, from about 50% to about 80% or about 50% to about 100%. In a particular embodiment, the dose is about 20% equimolar to the canonical nucleoside. In another particular embodiment, the dose is about 50% equimolar to the canonical nucleoside. In still another embodiment, the dose is about 100% equimolar to the canonical nucleoside.

Administration of the at least one prodrug or composition comprising the same can be once a day, twice a day, three times a day, four times a day, five times a day, up to six times a day, preferably at regular intervals. Doses can also be lowered if being administered intravenously or intrathecally. Preferred dose ranges for such administration are from about 50 mg/kg/day to about 500 mg/kg/day.

In embodiments wherein the composition comprises more than one prodrug, the ratio of the prodrugs can vary. For example, if two prodrugs are to be administered, they can be in a ratio of 50/50, or in ratios of about 5/95, 10/90, 15/85, 20/80, 25/75, 30/70, 35/65, 40/60, 45/55, 55/45, 60/40, 65/35, 70/30, 75/25, 80/20, 85/15, 90/10, and 95/5.

In one embodiment, the method further comprises monitoring the subject for improvement of their condition prior to increasing the dosage. A subject's response to the therapeutic administration can be monitored by observing a subject's muscle strength and control, and mobility as well as changes in height and weight. If one or more of these parameters increase after the administration, the treatment can be continued. If one or more of these parameters stays the same or decreases, the dosage can be increased.

In another embodiment, the method further comprises monitoring the subject for adverse reactions prior to decreasing the dosage. Exemplary adverse effects include, but are not limited to, diarrhea, abdominal bloating and other gastrointestinal manifestations.

The prodrugs of the present invention can also be co-administered with other agents. Such agents would include therapeutic agents for treating the symptoms of the particular form of MDS. In particular, for TK2 deficiency, other agents include an inhibitor of ubiquitous nucleoside catabolic enzymes, including but not limited to enzyme inhibitors such as tetrahydrouridine (inhibitor of cytidine deaminase) and immucillin H (inhibitor of purine nucleoside phosphorylase) and tipiracil (inhibitor of thymidine phosphorylase). Such inhibitors are known and used in the treatment of some cancers.

EXAMPLES

Example 1

Mouse Model of TK2 Deficiency

Effectiveness of prodrugs described herein was accessed via a mouse model. A homozygous Tk2 H126N knock-in mutant (Tk2$^{-/-}$) mouse that manifests a phenotype strikingly similar to the human infantile encephalomyopathy has been previously reported (Akman, et al. 2008). Between postnatal day 10 and 13, Tk2$^{-/-}$ mice rapidly develop fatal encephalomyopathy characterized by decreased ambulation, unstable gait, coarse tremor, growth retardation, and rapid progression to early death at age 14 to 16 days. Molecular and biochemical analyses of the mouse model demonstrated that the pathogenesis of the disease is due to loss of enzyme activity and ensuing dNTP pool imbalances with decreased dTTP levels in brain and both dTTP and dCTP levels in liver, which, in turn, produces mtDNA depletion and defects of respiratory chain enzymes containing mtDNA-encoded subunits, most prominently in the brain and spinal cord.

Prodrugs were administered in 50 µl of Esbilac milk formula for small pets (Pet-Ag) by daily oral gavage to Tk2 H126N knockin mice (Tk2$^{-/-}$) and aged matched controls (Tk2$^+$). A 50/50 mixture of 3 and 4 was dosed at 580 mg/kg/day. A 50/50 mixture of 5 and 6 was dosed from 120 mg/kg/day to 430 mg/kg/day.

All treatments were administered from post-natal day 4 to 29 days. At age 21 days, mice were separated from the mother and the treatment was continued by oral administration. Mutant and control Tk2$^+$ mice were weighted and observed closely for comparison.

Mice were followed and weighed daily (it has been previously observed that incapacity of gaining weight is the first sign of disease).

The prodrug mixtures extended survival of tk2−/− mice in an equipotent manner to cannonical nucleosides and had a non-statistically significant improvement on weight.

Example 2 dGK Deficient Patient Derived Fibroblasts

Prodrugs were tested in dGK deficient patient derived fibroblasts to determine their effect on mtDNA copy number. An advantage to working with dGK-deficient fibroblasts is that they spontaneously undergo mtDNA depletion after quiescence is induced without the addition of DNA damaging agents. It has been previously demonstrated that supplementing the cell culture medium with dGuo (50 µM) was sufficient to prevent this depletion. Cells were grown up to confluence. Quiescence was induced by reducing FBS in the medium to 0.1%. Three days later (day 0), we supplemented cell culture medium with 50 µM of dGuo (deoxyguanosine) or prodrug of the present invention. Cells were maintained in the same conditions up to 18 days with regular addition of fresh medium. mtDNA copy number was evaluated at different timepoints throughout the experiment (day 4, 9 and 18). Results were expressed as the mean+SD of experimental duplicates, and plotted as the mtDNA/nDNA ratios respect to the average values obtained for three untreated healthy controls cultured in parallel.

Equimolar concentrations of dGuo and the other dG prodrugs available (50 µM) were tested in parallel under similar conditions. Results showed that a 50/50 mixture of 7 and 8 at 50 µM prevented mtDNA depletion.

The invention claimed is:

1. A method for treating a mitochondrial DNA depletion syndrome (MDS) in a subject in need thereof comprising administering to the subject a therapeutically effective amount of at least one prodrug of Formula III:

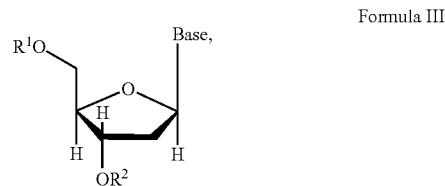

Formula III wherein Base refers to an optionally substituted heterocyclic base or an optionally substituted heterocyclic base with a protected amino group;
R$^1$ and R$^2$ are independent selected from hydrogen; phosphate; straight chained, branched, or cyclic alkyl; acyl; CO-alkyl; CO-alkoxyalkyl; CO-aryloxyalkyl; CO-substituted aryl; sulfonate ester; alkylsulfonyl; arylsulfonyl; aralkylsulfonyl; a lipid; a phospholipid; an amino acid; a carbohydrate; a peptide; and cholesterol; and wherein at least one of R$^1$ and R$^2$ is not hydrogen, and wherein R$^1$ and R$^2$ is not a modified phosphate.

2. The method of claim 1, wherein the prodrug is a compound of Formula IIIa:

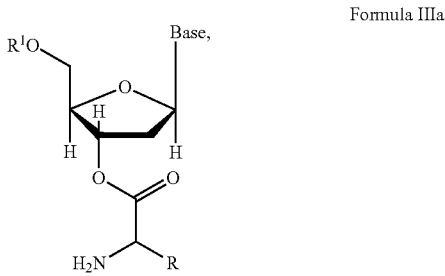

Formula IIIa wherein R is the side chain of an amino acid.

3. The method of claim 1, wherein at least two prodrugs are administered.

4. The method of claim 3, wherein the weight ratio of one prodrug to another prodrug is 50/50, 5/95, 10/90, 15/85, 20/80, 25/75, 30/70, 35/65, 40/60, 45/55, 55/45, 60/40, 65/35, 70/30, 75/25, 80/20, 85/15, 90/10 or 95/5.

5. The method of claim 1, wherein the prodrug is administered in the form of a pharmaceutical composition.

6. The method of claim 1, wherein the mitochondrial DNA depletion syndrome (MDS) is POLG or POLG2.

7. The method of claim 1, wherein the method of administration is oral.

8. The method of claim 1, wherein the therapeutically effective amount administered is from about 200 mg/kg/day to about 1,000 mg/kg/day.

9. The method of claim 1, wherein the prodrug or a composition comprising the prodrug is administered at least once per day.

10. The method of claim 1, wherein the dose administered is from about 200 mg/kg/day to about 1,000 mg/kg/day.

11. The method of claim 1, wherein the prodrug or composition comprising the same is administered at least once per day.

12. The method of claim 1, wherein the at least one prodrug is selected from the group consisting of:

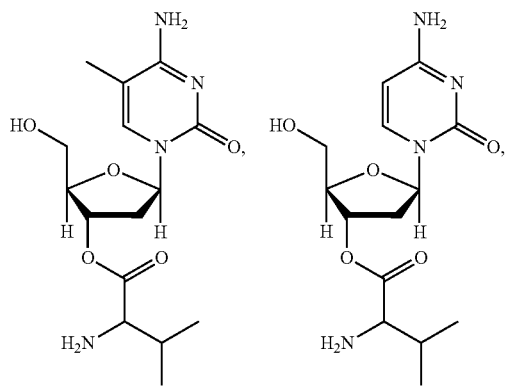

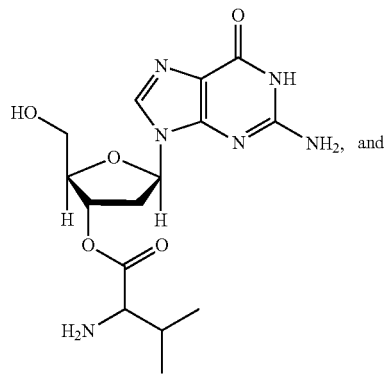

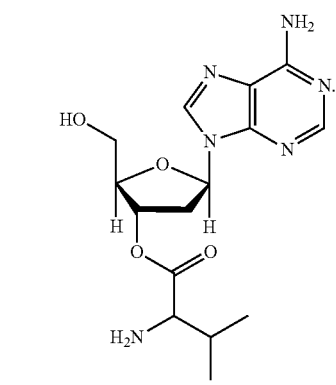

13. The method of claim 3, wherein the at least two prodrugs are:

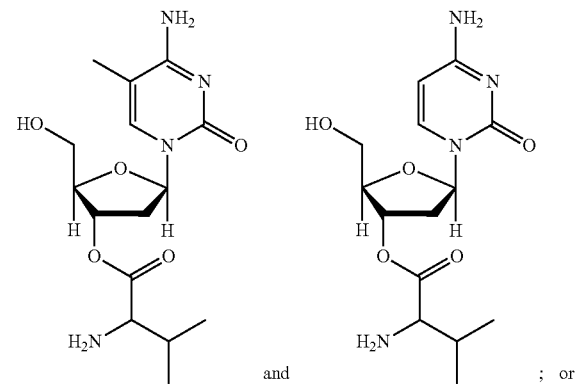

(i)

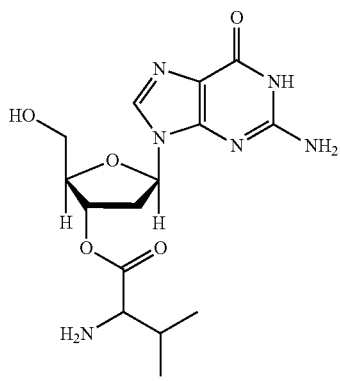

(ii)

and

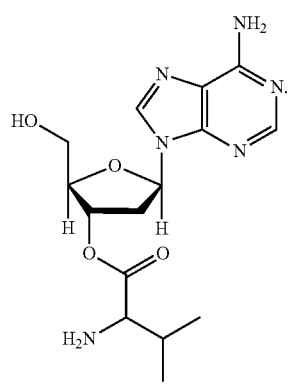

14. The method of claim 2, wherein Base is selected from the group consisting of cytosine, thymine, guanine, and adenine.

15. The method of claim 1, wherein $R^1$ and $R^2$ are CO-alkyl.

16. The method of claim 15, wherein alkyl is isopropyl.

17. The method of claim 1, wherein the prodrug is a compound of Formula IIIb:

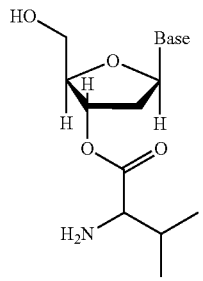

Formula IIIb wherein Base refers to an optionally substituted heterocyclic base or an optionally substituted heterocyclic base with a protected amino group.

18. The method of claim 17, wherein Base is selected from the group consisting of cytosine, thymine, guanine, and adenine.

19. The method of claim 1, wherein the prodrug is a compound of Formula IIIc:

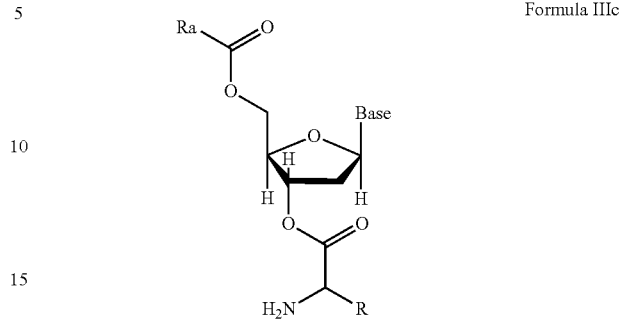

Formula IIIc wherein Base refers to an optionally substituted heterocyclic base or an optionally substituted heterocyclic base with a protected amino group;

Ra is selected from the group consisting of methyl, ethyl, n-propyl, isopropyl, n-butyl, sec-butyl, isobutyl, and tert-butyl; and R is $CH(CH_3)_2$.

20. The method of claim 19, wherein Ra is isopropyl.

21. The method of claim 20, wherein Base is selected from the group consisting of cytosine, thymine, guanine, and adenine.

* * * * *